(12) United States Patent
Bastin (10) Patent No.: US 10,028,732 B2
(45) Date of Patent: Jul. 24, 2018

(54) INTRALUMINAL OCCLUSION DEVICES AND METHODS OF BLOCKING THE ENTRY OF FLUID INTO BODILY PASSAGES

(71) Applicant: COOK MEDICAL TECHNOLOGIES LLC, Bloomington, IN (US)

(72) Inventor: Steve Bastin, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 286 days.

(21) Appl. No.: 14/946,814

(22) Filed: Nov. 20, 2015

(65) Prior Publication Data

US 2016/0074025 A1    Mar. 17, 2016

Related U.S. Application Data

(63) Continuation of application No. 12/976,323, filed on Dec. 22, 2010, now Pat. No. 9,211,123.

(60) Provisional application No. 61/291,437, filed on Dec. 31, 2009.

(51) Int. Cl.
*A61B 17/08* (2006.01)
*A61B 17/00* (2006.01)
*A61B 17/12* (2006.01)

(52) U.S. Cl.
CPC ...... *A61B 17/0057* (2013.01); *A61B 17/1215* (2013.01); *A61B 17/12022* (2013.01); *A61B 17/12027* (2013.01); *A61B 17/12031* (2013.01); *A61B 17/12122* (2013.01); *A61B 17/12145* (2013.01); *A61B 17/12172* (2013.01); *A61B 2017/00632* (2013.01); *A61B 2017/1205* (2013.01)

(58) Field of Classification Search
CPC ........ A61B 17/12022; A61B 17/12122; A61B 17/12172; A61B 17/12027; A61B 17/0057; A61B 17/12031; A61B 17/12145; A61B 17/1215; A61B 2017/00632; A61B 2017/1205
See application file for complete search history.

(56) References Cited

U.S. PATENT DOCUMENTS

| 5,449,373 | A | * | 9/1995 | Pinchasik | ............... | A61F 2/856 606/198 |
| 6,027,470 | A | * | 2/2000 | Mendius | ............. | A61F 9/00772 604/8 |
| 6,096,052 | A | * | 8/2000 | Callister | ................... | A61F 6/22 606/108 |
| 6,231,561 | B1 | | 5/2001 | Frazier et al. | | |
| 6,254,631 | B1 | | 7/2001 | Thompson | | |
| 6,261,319 | B1 | * | 7/2001 | Kveen | ....................... | A61F 2/91 623/1.15 |

(Continued)

*Primary Examiner* — Son Dang
(74) *Attorney, Agent, or Firm* — Buchanan Van Tuinen LLC (57) ABSTRACT

An intraluminal occlusion device includes a frame and an attached covering. The frame includes longitudinal struts having concave and convex portions. The intraluminal occlusion devices can be implanted at an opening to a body vessel, such as a blind passage, to block the entry of fluid into the vessel. Methods of blocking the entry of fluid into bodily passages are also described.

20 Claims, 4 Drawing Sheets

(56) References Cited

U.S. PATENT DOCUMENTS

| | | | |
|---|---|---|---|
| 6,589,276 B2* | 7/2003 | Pinchasik | A61F 2/856 623/1.16 |
| 6,635,083 B1* | 10/2003 | Cheng | A61F 2/91 623/1.15 |
| 6,746,477 B2* | 6/2004 | Moore | A61F 2/91 623/1.1 |
| 6,755,856 B2* | 6/2004 | Fierens | A61F 2/07 623/1.15 |
| 6,949,113 B2 | 9/2005 | Van Tassel et al. | |
| 6,994,092 B2* | 2/2006 | van der Burg | A61B 17/0057 128/887 |
| 7,011,671 B2 | 3/2006 | Welch | |
| 7,128,073 B1* | 10/2006 | van der Burg | A61B 17/0057 128/887 |
| 7,160,333 B2* | 1/2007 | Plouhar | A61F 2/0063 623/23.72 |
| 7,179,275 B2* | 2/2007 | McGuckin, Jr. | A61F 2/01 606/200 |
| 7,566,336 B2* | 7/2009 | Corcoran | A61B 17/0057 606/151 |
| 7,745,217 B2* | 6/2010 | Patel | A61L 26/0033 424/198.1 |
| 7,819,918 B2* | 10/2010 | Malaviya | A61B 17/064 623/14.12 |
| 2002/0019660 A1* | 2/2002 | Gianotti | A61F 2/91 623/1.15 |
| 2002/0058911 A1* | 5/2002 | Gilson | A61F 2/013 604/96.01 |
| 2002/0111647 A1* | 8/2002 | Khairkhahan | A61B 17/0057 606/200 |
| 2002/0165605 A1* | 11/2002 | Penn | A61F 2/91 623/1.15 |
| 2003/0130680 A1* | 7/2003 | Russell | A61F 2/01 606/200 |
| 2004/0093012 A1* | 5/2004 | Cully | A61F 2/013 606/200 |
| 2005/0234543 A1 | 10/2005 | Glaser et al. | |
| 2005/0273157 A1* | 12/2005 | Pinchasik | A61F 2/915 623/1.15 |
| 2006/0004436 A1* | 1/2006 | Amarant | A61F 2/88 623/1.15 |
| 2006/0200228 A1* | 9/2006 | Penn | A61F 2/82 623/1.15 |
| 2007/0073384 A1* | 3/2007 | Brown | A61F 2/91 623/1.16 |
| 2007/0135826 A1 | 6/2007 | Zaver et al. | |
| 2007/0225796 A1* | 9/2007 | Yadin | A61F 2/856 623/1.16 |
| 2008/0051888 A1* | 2/2008 | Ratcliffe | A61F 2/08 623/13.18 |
| 2008/0109071 A1* | 5/2008 | Shanley | A61F 2/91 623/1.42 |
| 2008/0200945 A1* | 8/2008 | Amplatz | A61B 17/0057 606/195 |
| 2009/0287300 A1* | 11/2009 | Dave | A61L 31/06 623/1.42 |
| 2010/0030314 A1* | 2/2010 | Case | A61F 2/2418 623/1.3 |
| 2011/0004289 A1* | 1/2011 | Oepen | A61F 2/91 623/1.15 |
| 2011/0160753 A1 | 6/2011 | Bastin | |

* cited by examiner

INTRALUMINAL OCCLUSION DEVICES AND METHODS OF BLOCKING THE ENTRY OF FLUID INTO BODILY PASSAGES

CROSS REFERENCE TO RELATED APPLICATION

This application is a continuation of U.S. patent application Ser. No. 12/976,323, filed on Dec. 22, 2010 and which claims priority to U.S. Provisional Application Ser. No. 61/291,437, filed on Dec. 31, 2009. The entire disclosure of each of these related applications is hereby incorporated into this disclosure.

FIELD

The invention relates generally to the field of medical devices. More particularly, the invention relates to intraluminal occlusion devices that can be used to block the entry of fluid into a passage. The invention also relates to methods of blocking the entry of fluid into bodily passages.

BACKGROUND

It is sometimes necessary or otherwise desirable to block the entry of fluid into a body passage. In some individuals, for example, the left atrial appendage (LAA), a relatively small, thumb-shaped cavity located off the left atrium between the mitral valve and the left pulmonary vein, may not contract with enough force to completely expel blood from the cavity as the heart contracts. The presence of stagnant blood in the LAA may increase the potential for the formation of blood clots and/or thrombi, which could lead to stroke and other clinical conditions.

Occlusion of the LAA may block the entry of blood into the LAA, thereby eliminating the presence of stagnant blood and reducing the potential for stroke and other clinical conditions.

A need exists, therefore, for improved intraluminal occlusion devices and methods of blocking the entry of fluid into bodily passages.

SUMMARY OF THE DISCLOSURE

Several exemplary intraluminal occlusion devices are described herein. The occlusion devices can be used to block the entry of fluid into a bodily passage.

An exemplary intraluminal occlusion device comprises a tubular frame having a lengthwise axis, a proximal end defining a proximal opening, a distal end defining a distal opening, and a circumferential surface extending from the proximal end to the distal end. The frame comprises two or more longitudinal struts, each of which has a proximal concave portion and a distal convex portion. A covering extends over the proximal opening and is attached to the tubular frame.

Another exemplary intraluminal occlusion device comprises a tubular frame having a lengthwise axis, a proximal end defining a proximal opening, a distal end defining a distal opening, and a circumferential surface extending from the proximal end to the distal end. A bioremodellable covering is attached to the frame and extends over the proximal opening. A first longitudinal strut has a first proximal concave portion and a first distal convex portion. The first proximal concave portion has a first longitudinal midpoint and the first distal convex portion has a second longitudinal midpoint. A first transverse axis orthogonally intersects the first proximal concave portion at the first longitudinal midpoint and a second transverse axis orthogonally intersects the first distal convex portion at the second longitudinal midpoint. The first transverse axis orthogonally intersects the longitudinal axis of the intraluminal occlusion device.

Another exemplary intraluminal occlusion device comprises a tubular frame having a lengthwise axis, a proximal end defining a proximal opening, a distal end defining a distal opening, and a circumferential surface extending from the proximal end to the distal end. A bioremodellable covering is attached to the frame and extends over the proximal opening. A first longitudinal strut has a first proximal concave portion and a first distal convex portion. The first proximal concave portion has a first longitudinal midpoint and the first distal convex portion has a second longitudinal midpoint. A first transverse axis orthogonally intersects the first proximal concave portion at the first longitudinal midpoint and a second transverse axis orthogonally intersects the first distal convex portion at the second longitudinal midpoint. The first transverse axis orthogonally intersects the longitudinal axis of the intraluminal occlusion device while the second transverse axis non-orthogonally intersects the longitudinal axis of the intraluminal occlusion device. A barb of a first series of barbs is disposed on the proximal end of the concave portion of one of the longitudinal struts and a barb of a second series of barbs is disposed on the distal end of the concave portion of one of the longitudinal struts.

Methods of blocking the entry of fluid into bodily passages are also described.

An exemplary method of blocking the entry of fluid into a bodily passage comprises delivering an intraluminal occlusion device according to the invention to an opening of the bodily passage into which the entry of fluid is to be blocked; positioning the intraluminal occlusion device at a point of treatment such that the proximal concave portions of the one or more longitudinal struts are adjacent the opening to the bodily passage being blocked, and such that the distal convex portions are disposed further within the bodily passage bodily passage being blocked; and anchoring the intraluminal occlusion device at the point of treatment.

An exemplary method of blocking the entry of fluid into the left atrium appendage of an animal, such as a human or other mammal, comprises delivering an intraluminal occlusion device according to the invention to an opening of the left atrium appendage into which the entry of fluid is to be blocked; positioning the intraluminal occlusion device at a point of treatment such that the proximal concave portions of the one or more longitudinal struts are adjacent the opening to the LAA, and such that the distal convex portions are disposed further within the LAA; deploying the intraluminal occlusion device from the delivery system at the point of treatment such that the tissue of the annular opening of the LAA contacts the proximal concave portions of the one or more longitudinal struts and such that the distal convex portions of the one or more longitudinal struts are disposed within the LAA and in contact with the tissue of the interior chamber defined by the LAA; and removing the delivery system from the bodily passage(s) through which it was navigated.

Additional understanding of the devices and methods contemplated and/or claimed by the inventor can be gained by reviewing the detailed description of exemplary embodiments, presented below, and the referenced drawings.

DETAILED DESCRIPTION OF EXEMPLARY EMBODIMENTS

The following description of exemplary embodiments provides illustrative examples of that which the inventor regards as his invention. As such, the embodiments discussed herein are merely exemplary in nature and are not intended to limit the scope of the invention, or its protection, in any manner. Rather, the description of these exemplary embodiments serves to enable a person of ordinary skill in the relevant art to practice the invention.

Figure 1:
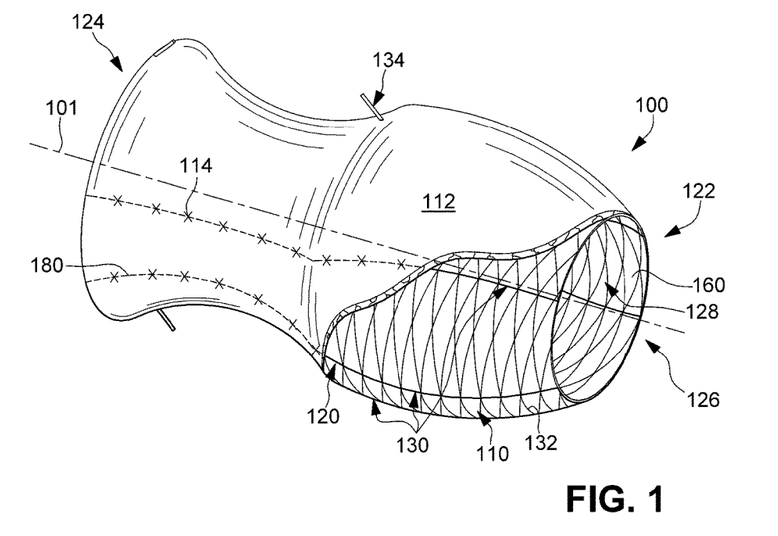
FIG. 1 is an isometric view, partially broken away, of a first exemplary intraluminal occlusion device.
Figure 2:
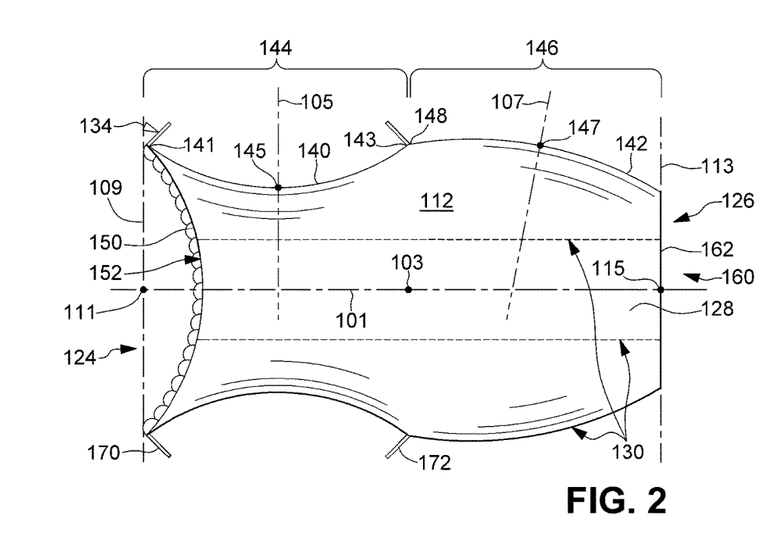
FIG. 2 is a sectional view of the intraluminal occlusion device illustrated in FIG. 1.
Figure 3:
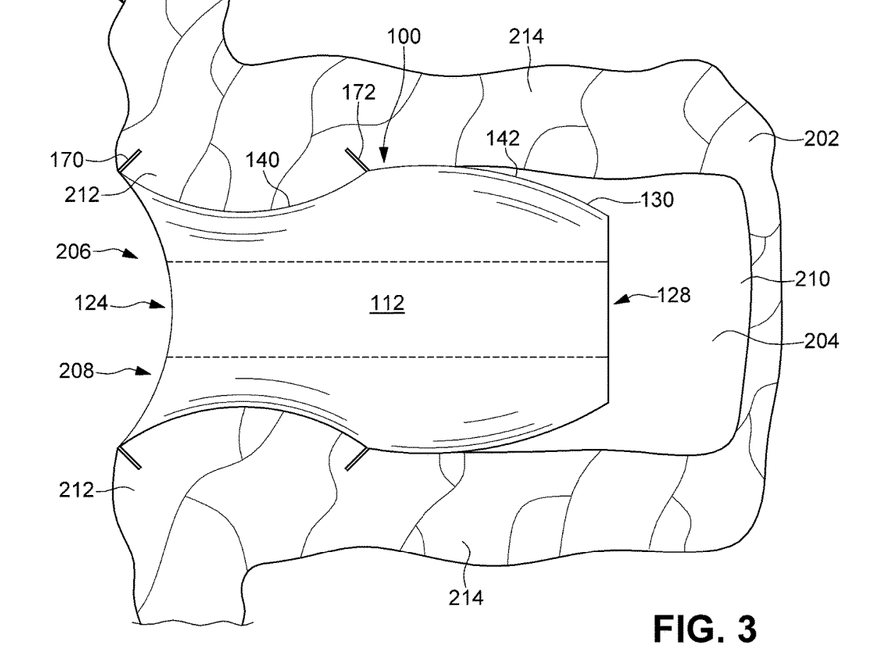
FIG. 3 is a sectional view of a left atrial appendage into which the intraluminal occlusion device illustrated in FIG. 1 has been implanted.

FIGS. 1 through 3 illustrate an expandable intraluminal occlusion device 100 according to a first embodiment. The occlusion device 100 comprises a frame 110 and a covering 112 attached to the frame 110 by a plurality of attachment elements 114.

FIG. 2 illustrates various references lines and points used herein in connection with describing various aspects of the expandable intraluminal occlusion device 100. The expandable intraluminal occlusion device 100 has a longitudinal axis 101 that includes longitudinal midpoint 103. The expandable intraluminal occlusion device 100 also has first 105 and second 107 transverse axes. These axes 105, 107 do not necessarily orthogonally intersect the longitudinal axis 101. Thus, as described more fully below, these axes 105, 107 do not necessarily intersect the longitudinal axis 101 at right angles. A proximal end axis 109 includes the proximal end of the frame 112 and orthogonally intersects the longitudinal axis 101 at proximal axial intersection point 111. Similarly, a distal end axis 113 includes the distal end of the frame 112 and orthogonally intersects the longitudinal axis 101 at distal axial point 115.

The frame 110 advantageously has radially compressed and radially expanded configurations, allowing the frame 110 to be implanted at a point of treatment within a body vessel by minimally invasive techniques. For example, the expandable nature of the frame 110 allows the intraluminal occlusion device 100 to be navigated through a body vessel on a delivery catheter while in a radially compressed configuration, and deployed at a point of treatment in a body vessel by transitioning from the radially compressed configuration to the radially expanded configuration. The transition from the radially compressed configuration to the radially expanded configuration can be accomplished according to conventional techniques, such as by removing a constraining force or by applying and outwardly-directed expansive force, as appropriate for the type of expandable frame used in an intraluminal occlusion device according to a particular embodiment (see below).

The frame 110 provides a void-filling function to the intraluminal occlusion devices described herein. The frame 110 can optionally provide additional function to these devices. For example, the frame 110 can provide a stenting function, i.e., exert a radially outward force on the interior wall of a vessel in which the intraluminal occlusion device 100 is implanted. By including a frame 110 that exerts such a force, an intraluminal occlusion device 100 can provide both a void-filling and a stenting function at a point of treatment within a body vessel. Expandable frames are considered advantageous for their ability to provide this additional stenting function.

The expandable frame 110 can be a self-expandable frame or a frame that requires the application of a force to effect expansion, such as a balloon-expandable frame. The structural characteristics of both of these types of support frames are known in the art, and are not detailed herein. Each type of expandable frame has advantages and for any given application, one type may be more desirable than the other based on a variety of considerations. For example, in the peripheral vasculature, vessels are generally more compliant and typically experience dramatic changes in their cross-sectional shape during routine activity. Intraluminal medical devices for implantation in the peripheral vasculature should retain a degree of flexibility to accommodate these changes of the vasculature. Accordingly, expandable intraluminal occlusion devices intended for implantation in the peripheral vasculature advantageously include a self-expandable support frame. These support frames, as is known in the art, are generally more flexible than balloon-expandable support frames following deployment.

If an ability to be delivered to and deployed at a point of treatment in a body vessel by minimally-invasive techniques is not a consideration, a non-expandable frame can be used in an intraluminal occlusion device according to an embodiment of the invention. For example, a frame formed of plastic, metal, or other suitable material and having little or no compliance can be used in intraluminal occlusion devices intended to be placed at a point of treatment using other techniques, such as surgical placement techniques.

Suitable frames can be made from a variety of materials and need only be biocompatible or able to be made biocompatible. Examples of suitable materials include, without limitation, stainless steel, nickel titanium (NiTi) alloys, e.g., nitinol, other shape memory and/or superelastic materials, molybdenum alloys, tantalum alloys, titanium alloys, precious metal alloys, nickel chromium alloys, cobalt chromium alloys, nickel cobalt chromium alloys, nickel cobalt chromium molybdenum alloys, nickel titanium chromium alloys, linear elastic Nitinol wires, polymers, and composite materials. Also, resorbable and bioremodellable materials can be used. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Stainless steel and nitinol are currently considered desirable materials for use in the support frame due at least to their biocompatibility, shapeability, ready commercial availability, and well-characterized nature. Also, cold drawn cobalt chromium alloys, such as ASTM F562 and ASTM F1058 (commercial examples of which include MP35N™ and Elgiloy™, both of which are available from Fort Wayne Metals, Fort Wayne, Ind.; MP35N is a registered trademark of SPS Technologies, Inc. (Jenkintown, Pa., USA); Elgiloy is a registered trademark of Combined Metals of Chicago LLC (Elk Grove Village, Ill., USA)), are currently considered advantageous materials for the support frame at least because they are non-magnetic materials that provide beneficial magnetic resonance imaging (MRI) compatibility, and avoid MRI artifacts typically associated with some other materials, such as stainless steel.

Suitable frames can also have a variety of shapes and configurations, including braided strands, helically wound strands, ring members, consecutively attached ring members, zig-zag members, tubular members, and frames cut from solid tubes.

Frames for use in the intraluminal occlusion devices described herein can be formed in a variety of manners. For example, the frame can be formed from one or more wires, such as from lengths of wire having a circular, D-shaped or other suitable cross-sectional configuration. Also, a frame can be cut from a tubular member, such as by cutting a desired pattern of struts from a tubular section of a suitable material. Laser-cutting a frame from a tubular section of nitinol, stainless steel or other material is considered an advantageous process for forming a frame for use in an intraluminal occlusion device according to a particular embodiment. A solid tubular member can also be used.

Furthermore, no matter the type of frame used in an intraluminal occlusion device according to a particular embodiment, the frame can include any suitable arrangement of struts.

In the embodiment illustrated in FIGS. 1 through 3, the frame 110 comprises an expandable frame having struts 120 that form a tubular structure 122 with proximal 124 and distal 126 ends. The frame defines an interior chamber 128 that is in communication with the external environment via spaces between the various struts 120. The frame 110 is a self-expandable frame that includes a plurality of longitudinal struts 130 and a plurality of interconnecting struts 132 that individually extend between adjacent longitudinal struts 130. The frame 110 also includes a series of barbs 134 adapted to engage adjacent tissue when the intraluminal occlusion device 100 is implanted at a point of treatment within a body vessel.

Each of the longitudinal struts 130 can have any suitable size, shape and configuration. The longitudinal struts 130 shown for the embodiment illustrated in FIGS. 1 through 3 include structural features that adapt the intraluminal occlusion device 100 for use in the left atrial appendage and other blind passages that include an annular opening.

As best illustrated in FIG. 2, each of the longitudinal struts 130 in this embodiment includes a concave portion 140 and a convex portion 142. The concave portion 140 of each longitudinal strut 130 has a proximal end 141 and a distal end 143, and a length 144 that extends along the longitudinal axis 101 from the proximal axial intersection point 111 to a point on the longitudinal axis 101 that is beyond the midpoint 103 of the longitudinal axis 101. In contrast, the convex portion 142 has a length 146 that extends along the longitudinal axis 101 from the distal axial intersection point 115 to a point on the longitudinal axis 101 that is before the midpoint 103. While the illustrated configuration is considered advantageous, it is understood that alternative relative configurations of the concave 140 and convex 142 portions of the longitudinal struts 130 are also contemplated. For example, the convex portion 142 of each longitudinal strut 130 can have a length that extends along the longitudinal axis 101 from the distal axial intersection point 115 to a point on the longitudinal axis 101 that is beyond the midpoint 103 of the longitudinal axis 101, giving the concave portion 140 a length that extends along the longitudinal axis 101 from the proximal axial intersection point 111 to a point on the longitudinal axis 101 that is before the midpoint 103.

Figure 4:
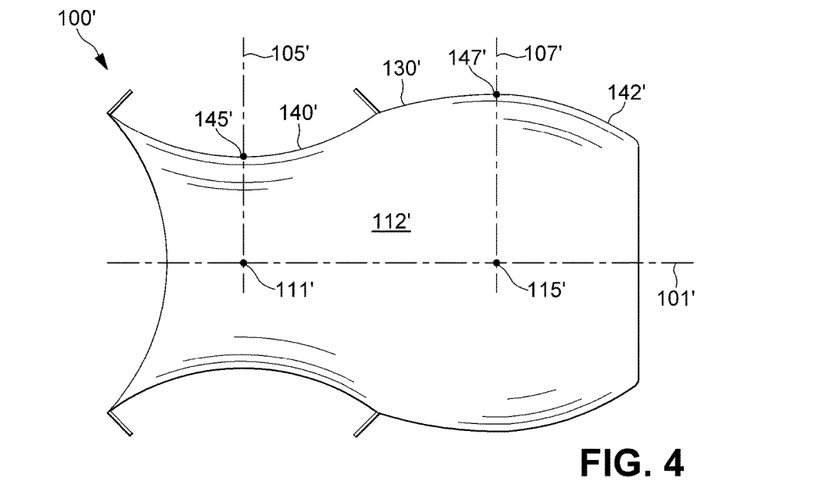
FIG. 4 is a sectional view of a second exemplary intraluminal occlusion device.

As best illustrated in FIG. 2, the first transverse axis 105 orthogonally intersects longitudinal strut 130 at the longitudinal midpoint 145 of the concave portion 140 and the second transverse axis 107 orthogonally intersects longitudinal strut 130 at the longitudinal midpoint 147 of the convex portion 142. In the first exemplary embodiment, the first transverse axis 105 also orthogonally intersects the longitudinal axis 101 when the frame 112 is in its fully expanded configuration (i.e., its resting state). The second longitudinal axis 107, however, intersects that longitudinal axis 101 in a non-orthogonal manner (i.e., not at ninety degrees). FIG. 4 illustrates an alternative embodiment in which the intraluminal occlusion device 100' includes first 105' and second 107' transverse axes that orthogonally intersect the longitudinal strut 130' at the longitudinal midpoints 145', 147' of the concave 140' and convex 142' portions, respectively, and that each orthogonally intersect the longitudinal axis 101'.

Each of these arrangements of the concave 140 and convex 142 portions of the longitudinal struts 130 has expected advantages, and a skilled artisan will be able to determine an appropriate arrangement for an expandable intraluminal occlusion device according to a particular embodiment based on various considerations. For example, the arrangement illustrated for the second exemplary embodiment (FIG. 4) is expected to confer an enhanced anchoring ability onto the frame 112, which may be beneficial in expandable intraluminal occlusion devices intended to be used in vessels within which it is relatively difficult to anchor a device immediately following deployment. This arrangement might also be beneficial in expandable intraluminal occlusion devices that lack a covering that contributes to the overall anchoring ability of the device (i.e., an expandable intraluminal occlusion device that includes a covering that resists tissue ingrowth, etc.).

While the concave 140 and convex 142 portions of the longitudinal struts 130 are illustrated as being directly adjacent each other, i.e., sharing common transition point 148, the two portions 140, 142 can be separated by another portion of the longitudinal strut 130, such as a linear or other curvilinear portion of the strut 130.

Any suitable number and arrangement of longitudinal struts 130 can be used in an intraluminal occlusion device according to a particular embodiment. To provide desirable structural properties, it is considered advantageous to include at least two longitudinal struts 130. It is considered particularly advantageous to include three or more longitudinal struts 130. As best illustrated in FIG. 1, an arrangement that positions three or more longitudinal struts 130 equidistant from the longitudinal axis 101 of the intraluminal occlusion device 100 is considered advantageous. In the embodiment illustrated in FIGS. 1 through 3, four longitudinal struts 130 are positioned equidistant from the longitudinal axis 101 and are evenly spaced about a circumference on a plane that orthogonally intersects the longitudinal axis 101.

Each of the interconnecting struts 132 in the embodiment illustrated in FIGS. 1 through 3 spans the space between immediately adjacent longitudinal struts 130. Adjacent interconnecting struts 132 intersect each other to form a crossing pattern. While linear interconnecting struts 132 are illustrated in the figures, other configurations can be used, including curvilinear struts, angulated struts, and struts with tapers, bends, fillets, and/or other structural features.

As best illustrated in FIG. 2, the proximal end 124 of the frame 112 includes curvilinear end struts 150 that extend between longitudinal struts 130. The end struts 150 define a concave proximal end 152 to which a portion of the covering 112 can be attached. Any suitable number, shape and configuration of struts can be used to form the concave proximal end 152 of the frame 110.

The inclusion of the concave proximal end 152 on the frame 110 is considered advantageous at least because it confers a concave proximal end onto the intraluminal occlusion device 100 once the covering 112 is attached to the frame 110. The covering 112 can be attached to the curvilinear end struts 150 so that the exterior surface of the covering follows the curvilinear surface defined by the curvilinear end struts 150, conferring a inward directed bowl-shape onto the proximal end of the expandable intraluminal occlusion device 100. This overall structure for the occlusion device 100 is considered advantageous at least because it provides a curvilinear surface that is expected to deflect fluid flow following implantation of the occlusion device 100 in a body vessel. A curvilinear surface is expected to minimize fluid impingement on the proximal end of the expandable intraluminal occlusion device 100, which may reduce or minimize the potential for clotting or other consequences following implantation of the occlusion device 100 in a blood-containing environment.

Figure 5:
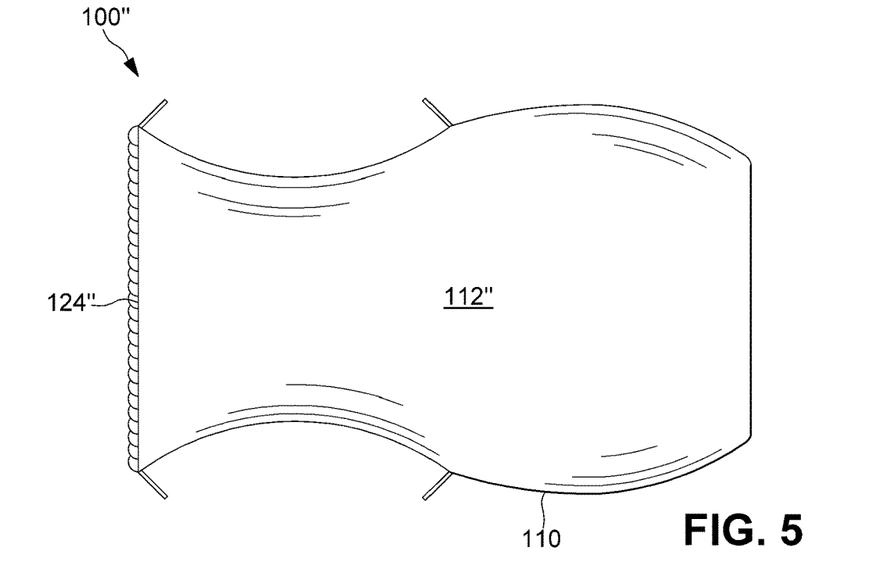
FIG. 5 is a sectional view of a third exemplary intraluminal occlusion device.

In an alternative embodiment, illustrated in FIG. 5, the intraluminal occlusion device 100" includes a covering 112" that is drawn taught across an opening defined by the proximal end 124" of the frame 110". This can be accomplished by including linear or substantially linear struts at the proximal end of the frame 110" and attaching the covering to these struts, by omitting struts across the proximal end 124" (leaving an opening) and positioning the cover 112" across the opening, or by leaving the covering unattached to curvilinear end struts, such as curvilinear end struts 150 of the embodiment illustrated in FIGS. 1 through 3. This arrangement might provide some "give" to the covering, which may aid in the flushing of fluid away from the proximal end of the occlusion device 100".

In contrast to the proximal end of the frame 110, the distal end 126 of the frame 110 in the first exemplary embodiment illustrated in FIGS. 1 through 3 is substantially flat. The frame 110 can include structural members that provide a flat surface on the distal end 126 or, as best illustrated in FIG. 1, the distal end 126 can simply comprise an opening 160. The covering 112 is placed across the opening 160 to provide a flat section 162 that is adapted to contact an opposing wall of the vessel into which the intraluminal occlusion device 100 is implanted. This structural configuration is considered advantageous at least because the flat section 162 of the covering 112 is expected to provide substantial surface area that can contribute to the overall contact between the covering 112 and the vessel wall, which may facilitate anchoring of the occlusion device following deployment. This is believed to be particularly advantageous in embodiments that include a bioremodellable covering because the ability of these coverings to integrate with surrounding tissue during the remodelling process is affected by the extent of surface-to-surface contact between the covering and the tissue.

The frame 110 of this embodiment also includes a series of barbs 134. While considered optional, inclusion of the barbs 134 is considered advantageous at least because they facilitate anchoring of the intraluminal occlusion device 100 in a body vessel following deployment. Any suitable barb structure can be used, including barbs integrally formed by the frame 110, separately attached barb members, and microbarb structures.

As best illustrated in FIG. 2, the barbs 134 of the first exemplary intraluminal occlusion device include first 170 and second 172 series of barbs. Each barb of the first series of barbs 170 is disposed on the proximal end 141 of the concave portion 140 of a longitudinal strut 130 and extends away from the longitudinal strut and toward the first transverse axis 105. Similarly, each barb of the second series of barbs 172 is disposed on the distal end 143 of the concave portion 140 of a longitudinal strut 130 and extends away from the longitudinal strut 130 and toward the first transverse axis 105.

This arrangement of barbs is considered particularly advantageous for inclusion in intraluminal occlusion devices intended for use in blind passages, such as the left atrial appendage, that have an annular opening from another vessel.

FIG. 3 illustrates the intraluminal occlusion device 100 implanted in a left atrial appendage (LAA) 200. The LAA 200 has a tissue wall 202 that defines a blind passage 204. A proximal end 206 defines an annular opening 208 while the distal end 210 is closed by the tissue wall 202.

The intraluminal occlusion device 100 is disposed within the LAA 200 such that the portion 212 of the tissue wall 202 that defines the annular opening 208 is in contact with the concave portions 140 of the longitudinal struts 130 of the intraluminal occlusion device 100. Barbs of the first 170 and second 172 of barbs extend into the portion 212 of the tissue wall 202 that defines the annular opening 208. Portions 214 of the tissue wall 202 that are distal to the portion 212 that defines the annular opening 208 are in contact with the convex portions 142 of the longitudinal struts 130 of the intraluminal occlusion device 100. This structural arrangement and relationship between the intraluminal occlusion device 100 and the LAA 200 is expected to provide suitable anchoring of the device 100.

FIG. 3 illustrates the curvilinear proximal end 124 of the intraluminal occlusion device 100 relative to the LAA 200. The curvilinear proximal end 124 provides an inward bowl-shaped surface relative to the substantially linear surface provided by the portion 212 of the tissue wall 202 that defines the annular opening 208. As described above, the presence of the inward bowl-shaped surface is expected to provide beneficial performance characteristics when the device 100 is implanted in this manner.

As indicated above, the frame 110 defines an interior chamber 128. In the illustrated intraluminal occlusion device 100, the attached covering 112 separates the interior chamber 128 from the external environment.

A wide variety of coverings is known in the medical technology arts, and any suitable covering can be used in an expandable intraluminal occlusion device according to a particular embodiment. The covering need only be able to be attached or otherwise connected to the expandable frame as described herein.

The covering comprises a section of material, such as a sheet, that is attached to the frame 110. The covering can be formed of any suitable material, and is advantageously biocompatible or able to be rendered biocompatible. The material can advantageously comprise a flexible material. Examples of suitable materials for the covering include natural materials, synthetic materials, and combinations of natural and synthetic materials. Examples of suitable natural materials include extracellular matrix (ECM) materials, such as small intestine submucosa (SIS), and other bioremodellable materials, such as bovine pericardium. Other examples of ECM materials that can be used include stomach submucosa, liver basement membrane, urinary bladder submucosa, tissue mucosa, and dura mater. Examples of suitable synthetic materials include polymeric materials, such as expanded polytetrafluoroethylene and polyurethane. ECM materials are particularly well-suited materials for use in the covering, at least because of their abilities to remodel and become incorporated into adjacent tissues, facilitating anchoring of an expandable intraluminal occlusion device at a point of treatment in a body vessel. These materials can provide a scaffold onto which cellular in-growth can occur, eventually allowing the material to remodel into a structure of host cells. It is noted that two or more different materials can be used to form the covering. For example, a bioremodellable material can be used to form a portion of the covering that extends along the circumferential wall of the tubular frame, which a non-thrombogenic, substantially non-thrombogenic, or relatively less thrombogenic material, such as a synthetic material, can be used to for a portion of the covering that extends across the proximal end of the device. Such a covering is expected to be advantageous at least because the first portion can facilitate anchoring of the device and the second portion can facilitate deflection of blood or other fluid from the exposed proximal end of the device.

The covering 112 can be attached to the frame 110 in any suitable manner and using any suitable means for attaching a covering to a frame, such as sutures, clips, and other mechanical attachment elements. Alternatively, bonding agents and/or techniques can be used, such as adhesives, heat sealing, tissue welding, and cross-linking. Furthermore, direct attachment of the covering to the expandable frame can be used. For example, the struts of the frame can be woven through the covering to create an attachment. Also, the frame can be embedded within the covering, such as by dipping and spraying a polymeric material onto the frame to form an attached covering. The specific manner in which a particular covering is attached to an intraluminal occlusion device according to a particular embodiment will depend at least upon the materials used in the covering and the expandable frame.

In the embodiment illustrated in FIGS. 1 through 3, the covering 112 comprises a sheet of bioremodellable material that is attached to the expandable frame 110 by a series of sutures 180 that pass through the thickness of the covering and around one or more struts 120 of the frame 110. In this first exemplary embodiment, the covering 112 extends over the entire frame 100, including the first 124 and second 126 ends, such that there is no direct communication between the interior chamber 128 and the external environment.

Figure 6:
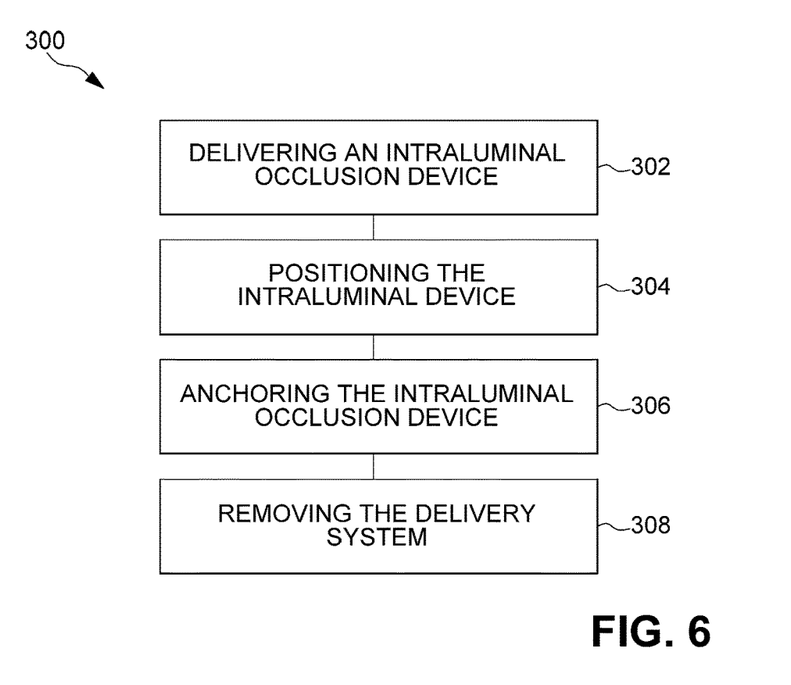
FIG. 6 is a flowchart representation of an exemplary method of blocking the entry of fluid into a bodily passage.

FIG. 6 illustrates a flow chart representation of a first exemplary method 300 of blocking the entry of fluid into a bodily passage. A first step 302 comprises delivering an intraluminal occlusion device according to the invention to an opening of the bodily passage into which the entry of fluid is to be blocked. In this exemplary method, the occlusion device includes one or more longitudinal struts, each having a proximal concave portion and a distal convex portion. The delivering step can be accomplished using minimally invasive and/or surgical techniques, and can be direct or through another body vessel that includes an opening to the bodily passage being blocked. If minimally-invasive techniques are used, the delivering step can include navigated an appropriate delivery system containing the occlusion device through the bodily passage being blocked, through another bodily passage that provides access to the bodily passage being blocked, or through another suitable route.

Another step 304 comprises positioning the intraluminal occlusion device at a point of treatment such that the proximal concave portions of the one or more longitudinal struts are adjacent the opening to the bodily passage being blocked, and such that the distal convex portions are disposed further within the bodily passage bodily passage being blocked.

Another step 306 comprises anchoring the intraluminal occlusion device at the point of treatment. For expandable intraluminal occlusion devices, the anchoring step can be accomplished by deploying the intraluminal occlusion device from an appropriate delivery system. For surgically placed occlusion devices, anchoring can also include attaching the device to the bodily passage, such as with sutures, clips, or other suitable attachment members.

An optional step 308 comprises removing the delivery system from the bodily passage(s) through which it was navigated, if a delivery system was used.

Figure 7:
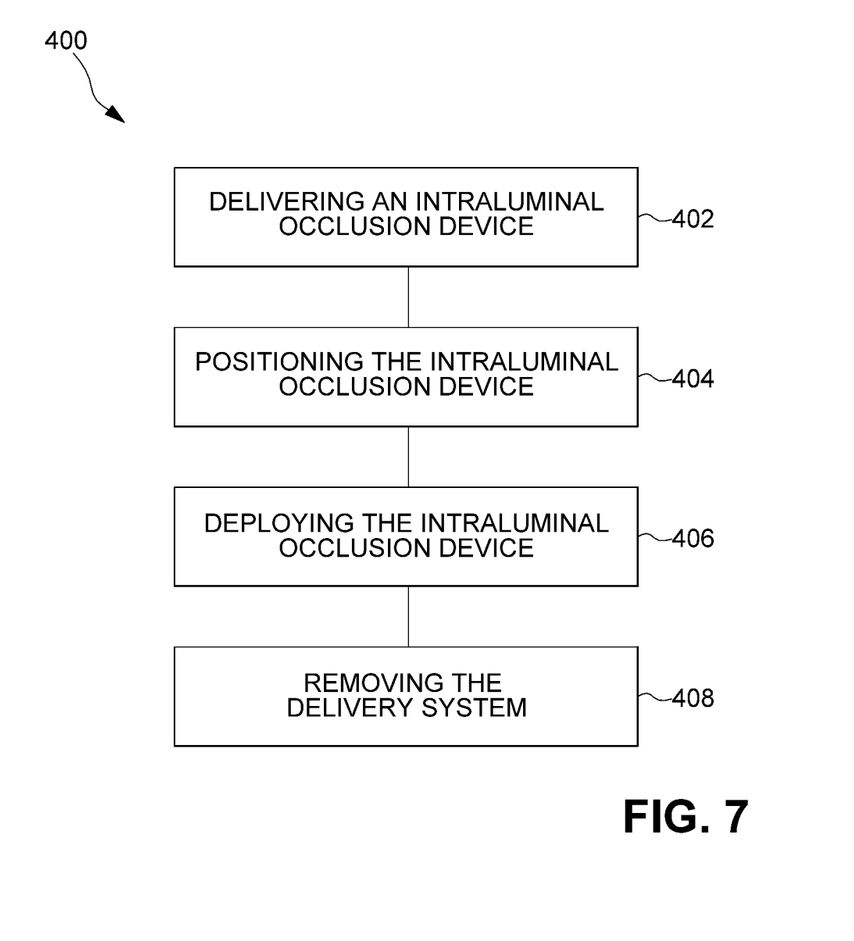
FIG. 7 is a flowchart representation of another exemplary method of blocking the entry of fluid into a bodily passage.

FIG. 7 illustrates a flow chart representation of an exemplary method 400 of blocking the entry of fluid into the left atrium appendage (LAA) of an animal, such as a human or other mammal.

A first step 402 comprises delivering an intraluminal occlusion device according to the invention to an opening of the LAA into which the entry of fluid is to be blocked. In this exemplary method, the occlusion device includes one or more longitudinal struts, each having a proximal concave portion and a distal convex portion. The occlusion device includes an expandable frame and is provided on a delivery system. In this exemplary method, the delivery system is navigated through one or more body vessels providing access to the LAA.

Another step 404 comprises positioning the intraluminal occlusion device at a point of treatment such that the proximal concave portions of the one or more longitudinal struts are adjacent the opening to the LAA, and such that the distal convex portions are disposed further within the LAA.

Another step 406 comprises deploying the intraluminal occlusion device from the delivery system at the point of treatment such that the tissue of the annular opening of the LAA contacts the proximal concave portions of the one or more longitudinal struts and such that the distal convex portions of the one or more longitudinal struts are disposed within the LAA and in contact with the tissue of the interior chamber defined by the LAA.

Another step 408 comprises removing the delivery system from the bodily passage(s) through which it was navigated.

The foregoing detailed description provides exemplary embodiments of the invention and includes the best mode for practicing the invention. The description and illustration of embodiments is intended only to provide examples of the invention, and not to limit the scope of the invention, or its protection, in any manner.

I claim:

1. An intraluminal occlusion device having a longitudinal axis, comprising:
   a tubular frame having a proximal end defining a proximal opening, a distal end defining a distal opening, and a circumferential surface extending from the proximal end to the distal end, the frame comprising two or more longitudinal struts and a plurality of interconnecting struts extending between adjacent longitudinal struts, each of the longitudinal struts having a proximal concave portion disposed within a plane that includes said longitudinal axis and a distal convex portion disposed within the plane that include said longitudinal axis; and
   a covering extending over the proximal opening and attached to the tubular frame.

2. The intraluminal occlusion device of claim 1, wherein the tubular frame comprises an expandable frame having radially compressed and radially expanded configurations.

3. The intraluminal occlusion device of claim 2, wherein the tubular frame comprises a self-expandable frame.

4. The intraluminal occlusion device of claim 2, wherein the tubular frame requires the input of an expansive force to transition from the radially compressed configuration to the radially expanded configuration.

5. The intraluminal occlusion device of claim 2, wherein the tubular frame is formed from one or more wires.

6. The intraluminal occlusion device of claim 2, wherein the tubular frame is cut from a tubular member.

7. The intraluminal occlusion device of claim 2, wherein the tubular frame comprises stainless steel.

8. The intraluminal occlusion device of claim 2, wherein the tubular frame comprises nitinol.

9. The intraluminal occlusion device of claim 1, wherein a first longitudinal strut has a first proximal concave portion and a first distal convex portion;
   wherein the first proximal concave portion has a first length that extends along said longitudinal axis of said intraluminal occlusion device and the first distal convex portion has a second length that extends along said longitudinal axis of said intraluminal occlusion device; and
   wherein the first length is greater than the second length.

10. The intraluminal occlusion device of claim 1, wherein a first longitudinal strut has a first proximal concave portion and a first distal convex portion;
    wherein the first proximal concave portion has a first longitudinal midpoint and the first distal convex portion has a second longitudinal midpoint;
    wherein a first transverse axis orthogonally intersects the first proximal concave portion at the first longitudinal midpoint;
    wherein a second transverse axis orthogonally intersects the first distal convex portion at the second longitudinal midpoint;
    wherein each of the first and second transverse axes orthogonally intersects said longitudinal axis of said intraluminal occlusion device.

11. The intraluminal occlusion device of claim 1, wherein the covering comprises a bioremodellable material.

12. The intraluminal occlusion device of claim 11, wherein the covering comprises an extracellular matrix material.

13. The intraluminal occlusion device of claim 12, wherein the covering comprises small intestine submucosa.

14. The intraluminal occlusion device of claim 1, wherein the covering extends over the circumferential surface defined by the tubular frame.

15. The intraluminal occlusion device of claim 14, wherein the covering extends over the distal opening.

16. The intraluminal occlusion device of claim 1, wherein the tubular frame includes one or more barbs disposed on a concave portion of at least one of the longitudinal struts.

17. The intraluminal occlusion device of claim 1, wherein the proximal concave portion of each of the longitudinal struts has a concave portion proximal end and a concave portion distal end;
    further comprising first and second series of barbs, each barb of the first series of barbs disposed on the concave portion proximal end of one of the longitudinal attachment struts and each barb of the second series of barbs disposed on the concave portion distal end of one of the longitudinal attachment struts;
    wherein each barb of the first and second series of barbs extends away from the one of the longitudinal attachment struts and radially outward with respect to said longitudinal axis of said intraluminal occlusion device.

18. An intraluminal occlusion device having a longitudinal axis, comprising:
    a tubular frame having a proximal end defining a proximal opening, a distal end defining a distal opening, and a circumferential surface extending from the proximal end to the distal end, the frame comprising two or more longitudinal struts and a plurality of interconnecting struts extending between adjacent longitudinal struts, each of the longitudinal struts having a proximal concave portion disposed within a plane that includes said longitudinal axis and a distal convex portion disposed within the plane that include said longitudinal axis; and
    a covering extending over the proximal opening and attached to the tubular frame;
    wherein a first longitudinal strut has a first proximal concave portion and a first distal convex portion;
    wherein the first proximal concave portion has a first length that extends along said longitudinal axis of said intraluminal occlusion device and the first distal convex portion has a second length that extends along said longitudinal axis of said intraluminal occlusion device;
    wherein the first length is greater than the second length; and
    wherein the covering extends over the circumferential surface defined by the tubular frame.

19. The intraluminal occlusion device of claim 18, wherein the covering extends over the distal opening.

20. An intraluminal occlusion device having a longitudinal axis, comprising:
    a tubular frame having a proximal end defining a proximal opening, a distal end defining a distal opening, and a circumferential surface extending from the proximal end to the distal end, the frame comprising two or more longitudinal struts and a plurality of interconnecting struts extending between adjacent longitudinal struts, each of the longitudinal struts having a proximal concave portion disposed within a plane that includes said longitudinal axis and a distal convex portion disposed within the plane that include said longitudinal axis; and
    a covering extending over the proximal opening and attached to the tubular frame;
    wherein a first longitudinal strut has a first proximal concave portion and a first distal convex portion;
    wherein the first proximal concave portion has a first longitudinal midpoint and the first distal convex portion has a second longitudinal midpoint;

wherein a first transverse axis orthogonally intersects the first proximal concave portion at the first longitudinal midpoint;

wherein a second transverse axis orthogonally intersects the first distal convex portion at the second longitudinal midpoint;

wherein each of the first and second transverse axes orthogonally intersects said longitudinal axis of said intraluminal occlusion device;

wherein the covering extends over the circumferential surface defined by the tubular frame; and wherein the covering extends over the distal opening.

* * * * *